(12) United States Patent
Goeken et al.

(10) Patent No.: US 8,034,066 B2
(45) Date of Patent: Oct. 11, 2011

(54) MULTI-LAYER MEDICAL BALLOONS

(75) Inventors: Kara Goeken, Dudley, MA (US);
Raymond Lareau, Westford, MA (US);
Fuh-Sheng Chen, San Diego, CA (US);
Show-Mean Wu, San Diego, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1154 days.

(21) Appl. No.: 11/228,854

(22) Filed: Sep. 15, 2005

(65) Prior Publication Data
US 2007/0060863 A1 Mar. 15, 2007

(51) Int. Cl.
*A61B 17/22* (2006.01)

(52) U.S. Cl. .............. 606/159; 604/103.08; 604/103.06

(58) Field of Classification Search ................ 606/159, 606/194; 604/22, 103.06, 103.08, 523
See application file for complete search history.

(56) References Cited

U.S. PATENT DOCUMENTS

| | | | |
|---|---|---|---|
| 4,963,313 A | 10/1990 | Noddin et al. | |
| 5,035,249 A * | 7/1991 | Sasaki et al. | 128/899 |
| 5,195,969 A * | 3/1993 | Wang et al. | 604/96.01 |
| 5,196,024 A | 3/1993 | Barath | |
| 5,209,799 A | 5/1993 | Vigil | |
| 5,270,086 A * | 12/1993 | Hamlin | 428/35.2 |
| 5,320,634 A * | 6/1994 | Vigil et al. | 606/159 |
| 5,336,234 A * | 8/1994 | Vigil et al. | 606/159 |
| 5,624,433 A | 4/1997 | Radisch, Jr. | |
| 5,714,110 A | 2/1998 | Wang et al. | |
| 5,797,877 A * | 8/1998 | Hamilton et al. | 604/96.01 |
| 6,013,055 A | 1/2000 | Bampos et al. | |
| 6,120,364 A | 9/2000 | Laflamme | |
| 6,132,824 A | 10/2000 | Hamlin | |
| 6,146,356 A * | 11/2000 | Wang et al. | 604/96.01 |
| 6,171,278 B1 * | 1/2001 | Wang et al. | 604/104 |
| 6,951,675 B2 | 10/2005 | Chin et al. | |
| 2002/0165523 A1 * | 11/2002 | Chin et al. | 604/523 |
| 2003/0163148 A1 * | 8/2003 | Wang et al. | 606/159 |
| 2003/0216668 A1 * | 11/2003 | Howland et al. | 600/585 |
| 2004/0034384 A1 | 2/2004 | Fukaya | |
| 2004/0133223 A1 | 7/2004 | Weber | |
| 2004/0146670 A1 | 7/2004 | Chin et al. | |
| 2005/0149102 A1 | 7/2005 | Radisch, Jr. et al. | |
| 2005/0261721 A1 | 11/2005 | Radisch, Jr. et al. | |

FOREIGN PATENT DOCUMENTS

| | | |
|---|---|---|
| EP | 0 582 870 A2 | 2/1994 |
| WO | WO 92/19316 | 11/1992 |
| WO | WO 03/072178 A1 | 9/2003 |

OTHER PUBLICATIONS

International Search Report and Written Opinion PCT/US2006/031923; mailed Dec. 28, 2006.
U.S. Appl. No. 09/950,195, entitled "Medical Balloon," and Filed Sep. 10, 2001.
U.S. Appl. No. 11/060,151, entitled "Medical Devices," and Filed Feb. 17, 2005.

* cited by examiner

*Primary Examiner* — Anhtuan Nguyen
*Assistant Examiner* — Julie A Szpira
(74) *Attorney, Agent, or Firm* — Seager Tufte Wickhem LLC

(57) ABSTRACT

The invention relates to multi-layer medical balloons. In one aspect, a medical device includes an inflatable balloon. The inflatable balloon includes a first layer including a material having a first modulus of elasticity, and a second layer adjacent the first layer, the second layer including a material having a second modulus of elasticity that differs from the first modulus of elasticity by at least about 2,000 psi. A cutting element is carried by the balloon.

16 Claims, 2 Drawing Sheets

US 8,034,066 B2

MULTI-LAYER MEDICAL BALLOONS

TECHNICAL FIELD

This invention relates to multi-layer medical balloons.

BACKGROUND

Balloon catheters can be used for a variety of medical procedures such as, for example, to widen an occluded body vessel, as in angioplasty, to position a medical device, such as a stent or a graft, or to selectively block a passageway. A balloon catheter may include an inflatable and deflatable balloon positioned on a long and narrow catheter body. Initially, the balloon is folded around the catheter body to reduce the radial profile of the balloon catheter for easy insertion into the body.

During use, for example, in angioplasty, the folded balloon can be positioned at a location in a vessel occluded by a stenosis by threading the balloon catheter through a guide catheter and over a guide wire emplaced in the body. The balloon is then inflated, e.g., by introducing a fluid into the interior of the balloon. Inflating the balloon can radially expand the stenosis so that the vessel can permit an increased rate of blood flow. After use, the balloon is deflated and withdrawn from the body.

In some cases, it is desirable to incise at least a portion of the stenosis, e.g., after or upon inflating the balloon. Incising the stenosis can further widen the body vessel and increase the rate of blood flow.

SUMMARY

The invention relates to multi-layer medical balloons.

In one aspect, the invention features a medical device including an inflatable balloon and a cutting element carried by the balloon. The inflatable balloon includes a first layer including a material having a first modulus of elasticity, and a second layer adjacent the first layer. The second layer includes a material having a second modulus of elasticity that differs from the first modulus of elasticity by at least about 2,000 psi.

Embodiments may include one or more of the following features.

In some embodiments, the second modulus of elasticity differs from the first modulus of elasticity by at least about 5,000 psi (e.g., at least about 10,000 psi, at least about 50,000 psi, at least about 100,000 psi).

In certain embodiments, the second modulus of elasticity differs from the first modulus of elasticity by at least about 50 percent (e.g., at least about 100 percent, at least about 500 percent) of the first modulus of elasticity.

In some embodiments, the first layer is disposed outwardly of the second layer.

In certain embodiments, an inner surface of the first layer is attached to an outer surface of the second layer.

In some embodiments, the inner surface of the first layer is bonded to the outer surface of the second layer.

In certain embodiments, the inner surface of the first layer is adhesively attached to the outer surface of the second layer.

In some embodiments, the first layer has a hardness less than a hardness of the second layer.

In certain embodiments, the first modulus of elasticity is less than the second modulus of elasticity.

In some embodiments, the cutting element is secured to an outer surface of the first layer.

In certain embodiments, the medical device further includes at least a third layer disposed inwardly of the second layer. The third layer has a third modulus of elasticity that differs from the second modulus of elasticity by at least about 2,000 psi.

In some embodiments, the third modulus of elasticity is less than the second modulus of elasticity.

In certain embodiments, the third modulus of elasticity is substantially equal to the first modulus of elasticity.

In some embodiments, the first and third layers are formed of the same material.

In certain embodiments, each of the first and second layers has a thickness of about one micron to about 50 microns.

In some embodiments, the thickness of the second layer is greater than the thickness of the first layer.

In certain embodiments, the thicknesses of the first and second layers are substantially equal.

In some embodiments, the inflatable balloon comprises at least five layers (e.g., at least about ten layers, at least about 15 layers, at least about 20 layers).

In certain embodiments, each of the at least five layers (e.g., at least about ten layers, at least about 15 layers, at least about 20 layers) has a modulus of elasticity that differs from an adjacent layer by at least about 2,000 psi.

In some embodiments, the inflatable balloon has a burst pressure of about ten atmospheres to about 30 atmospheres.

In certain embodiments, the inflatable balloon has compliance of about one percent to about 15 percent.

In some embodiments, the inflatable balloon is co-extruded.

Embodiments may include one or more of the following advantages.

Generally, the balloon includes multiple layers. This can help to prevent defects, such as cracks, from propagating between adjacent layers of the balloon. Consequently, the physical integrity of the balloon can be improved.

In certain embodiments, adjacent layers of the balloon have differing physical properties (e.g., differing moduli of elasticity). This can further help to prevent defects, such as cracks, within the balloon from propagating between adjacent layers.

Other aspects, features, and advantages will be apparent from the description, the drawings, and the claims.

DETAILED DESCRIPTION

Figure 1:
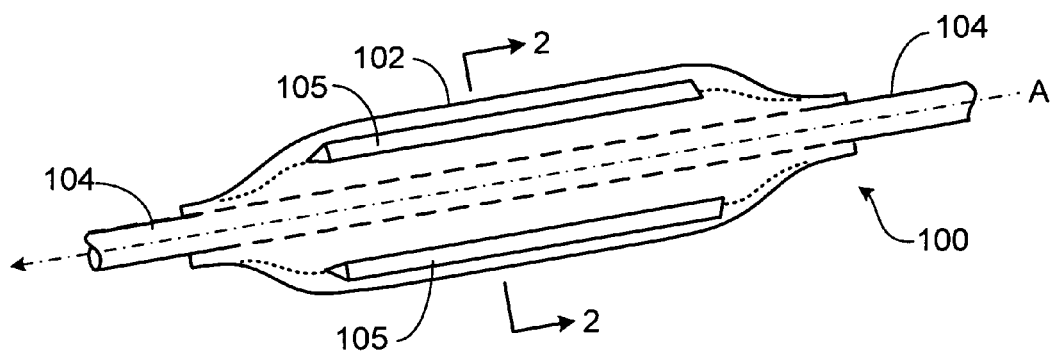
FIG. 1 is a perspective view of an embodiment of a balloon catheter.

As shown in FIG. 1, a balloon catheter 100 includes a catheter body 104, an inflatable balloon 102 attached to catheter body 104, and cutting elements 105 secured to an outer surface of balloon 102, for example, by an adhesive such as urethane. Medical devices such as balloon catheter 100 are described in, for example, U.S. Pat. Nos. 5,195,969 and 5,270,086, both hereby incorporated by reference. Cutting elements 105 are elongated members (e.g., steel blades) having a triangular cross-section in which the base is attached to balloon 102 and a cutting edge is formed at the apex of the triangular section. Examples of cutting elements are described, for example, in U.S. Pat. Nos. 5,209,799 and 5,336,234, and in Patent Application Publication No. US 2004/0133223, which are incorporated by reference herein.

Figure 2:
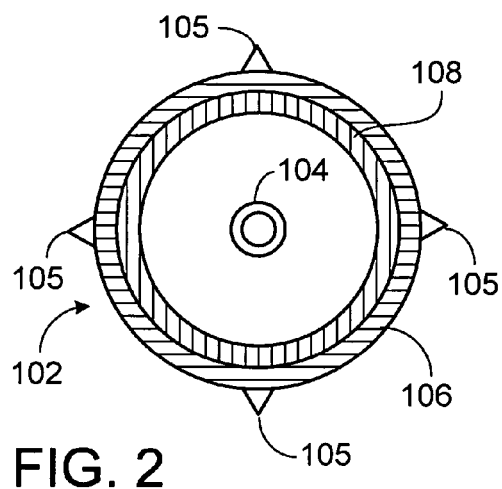
FIG. 2 is a cross-sectional view of the balloon catheter of FIG. 1, taken along line 2-2.

Referring to FIG. 2, balloon 102 can be co-extruded, and includes a first layer 106 (e.g., an outer layer) and a second layer 108 (e.g., an adjacent inner layer). The multiple layers (in this case two layers) can help to distribute stresses and divert defects, such as cracks or punctures, so that they are less likely to propagate through the balloon wall to the point of causing a failure.

First and second layers 106 and 108 have differing physical properties. The differing physical properties between the adjacent layers can further help to prevent propagation of defects within balloon 102. In some embodiments, first layer 106 (e.g., the material from which first layer 106 is formed) has a modulus of elasticity that differs from the modulus of elasticity of second layer 108 (e.g., the material from which second layer 108 is formed) by at least about 2,000 psi (e.g., at least about 5,000 psi, at least about 10,000 psi, at least about 25,000 psi, at least about 50,000 psi, at least about 75,000 psi, at least about 100,000 psi). The modulus of elasticity of second layer 108 can, for example, differ from the modulus of elasticity of first layer 106 by at least about 50 percent (e.g., 100 percent, 150 percent, 200 percent, 250 percent, 300 percent, 350 percent, 400 percent, 450 percent, 500 percent) of the modulus of elasticity of first layer 106.

Without wishing to be bound by theory, it is believed that the interface between adjacent layers 106 and 108 can dissipate energy, which can help to prevent defects within balloon 102 (e.g., defects originating near cutting members 105) from propagating between the adjacent layers. It is further believed that, relative to adjacent layers having similar moduli of elasticity, adjacent layers having differing moduli of elasticity, such as first layer 106 and second layer 108, require an increased amount of energy to allow propagation of a crack from one of the layers into the adjacent layer. This increase in energy can be especially significant where the layer into which the crack is attempting to propagate has a higher modulus of elasticity than the adjacent layer from which the crack is traveling. It is believed that the discontinuity of material stiffness at the layer interface can allow the crack to move along the boundary interface rather than across to the adjoining layer, which creates a longer path for crack propagation that will ultimately dissipate more energy and halt crack growth. It is further believed that, in addition to retarding growth and propagation of the crack, these arrangements can dissipate energy around the tip (e.g., the forwardmost point) of the crack.

In some embodiments, the modulus of elasticity of first layer 106 is less than the modulus of elasticity of second layer 108. First layer 106 can, for example, have a modulus of elasticity of about 20,000 psi to about 305,000 psi. In some embodiments, first layer 106 has a modulus of elasticity of about 20,000 psi (e.g., about 50,000 psi, about 100,000 psi, about 125,000 psi, about 150,000 psi, about 175,000 psi, about 200,000 psi, about 225,000 psi, about 250,000 psi, about 275,000 psi, about 300,000 psi) or greater, and/or about 300,000 psi (e.g., about 275,000 psi, about 250,000 psi, about 225,000 psi, about 200,000 psi, about 175,000 psi, about 150,000 psi, about 125,000 psi, about 100,000 psi, about 50,000 psi) or less.

Second layer 108 can have a modulus of elasticity of about 200,000 psi to about 600,000 psi. In certain embodiments, second layer 108 has a modulus of elasticity of about 200,000 psi (e.g, about 250,000 psi, about 300,000 psi, about 350,000 psi, about 400,000 psi, about 450,000 psi, about 500,000 psi, about 550,000 psi) or greater, and/or about 600,000 psi (e.g., about 550,000 psi, about 500,000 psi, about 450,000 psi, about 400,000 psi, about 350,000 psi, about 300,000 psi, about 250,000 psi) or less.

In some embodiments, first layer 106 is relatively soft and second layer 108 is relatively hard. This can further assist distribution of stress and retard defect propagation within balloon 102, while still providing relatively high burst strength and relatively low distention. The relatively soft first layer 106 can, for example, help to absorb and distribute stress imposed by cutting elements 105, while the relatively hard second layer 108 can help to provide balloon 102 with high burst strength and low distention. It is often desirable that the difference in hardness of adjacent bonded layers is about 40 Shore D or less, preferably 20 Shore D or less, which can enhance compatibility between the layers and reduce delamination at the interface. Hardness can be measured according to ASTM D2240. In some embodiments, second layer 108 has a hardness of more than about 60 Shore D (e.g., about 65 Shore D or more). In certain embodiments, first layer 106 has a hardness of about 60 Shore D or less. In some embodiments, first layer 106 has a hardness of greater than about 60 Shore D, but still softer than second layer 108.

In some embodiments, first layer 106 and second layer 108 are formed of Pebax 7033 and Nylon 12 (L2101F), respectively. In certain embodiments, first layer 106 and second layer 108 are formed of Nylon 12 (L2101F) and Nylon 612 (D22), respectively. In some embodiments, first layer 106 and second layer 108 are formed of Nylon 612 (D22) and PET, respectively.

While several examples of polymers and polymer combinations have been described above, any of various materials having differing physical properties (e.g., differing moduli of elasticity and/or different hardnesses) can be used to form layers 106 and 108. Examples of materials that can be used to form first layer 106 and/or second layer 108 include polyurethanes and block copolymers, such as polyamide-polyether block copolymers or amide-tetramethylene glycol copolymers. Examples include the PEBAX® (a polyamide/polyether/polyester block copolymer) family of polymers, e.g., PEBAX® 70D, 72D, 2533, 5533, 6333, 7033, or 7233 (available from Elf AtoChem, Philadelphia, Pa.). Other examples include nylons, such as aliphatic nylons, for example, Vestamid L2101F, Nylon 11 (Elf Atochem), Nylon 6 (Allied Signal), Nylon 6/10 (BASF), Nylon 6/12 (Ashley Polymers), or Nylon 12. Additional examples of nylons include aromatic nylons, such as Grivory (EMS) and Nylon MXD-6. Other nylons and/or combinations of nylons can be used. Still other examples include polybutylene terephthalate (PBT), such as CELANEX® (available from Ticona, Summit, N.J.), polyester/ether block copolymers such as ARNITEL® (available from DSM, Erionspilla, Ind.), e.g., ARNITEL® EM740, aromatic amides such as Trogamid (PA6-3-T, Degussa), and thermoplastic elastomers such as HYTREL® (Dupont de Nemours, Wilmington, Del.). In some embodiments, PEBAX®, HYTREL®, and ARNITEL® have a Shore D hardness of about 45D to about 82D.

The materials can be used pure or as blends. For example, a blend may include a PBT and one or more PBT thermoplastic elastomers, such as RITEFLEX® (available from Ticona), ARNITEL®, or HYTREL®, or polyethylene terephthalate (PET) and a thermoplastic elastomer, such as a PBT thermoplastic elastomer.

The materials can include one or more liquid crystal polymers (LCPs). Examples of LCPs include polyester(s), polyamide(s), their blends, and/or their copolymers, such as VECTRA® A (Ticona), VECTRA® B (Ticona), VECTRA® LKX (Ticona) (e.g., VECTRA® LKX 1107, 1111 (Ticona)), and VECTRAN® (e.g., VECTRAN V300P (Ticona)). Other LCPs and/or combinations of LCPs can be used.

In some embodiments, the materials may include an additive that decreases compliancy. The additive can be a pigment that reinforces the balloon material. Examples of additives include inorganic additives such as titanium oxides, such as $TiO_2$, calcium carbonate, mica, aramide fibers, carbon black, glass, or fiberglass.

In some embodiments, a compatibilizing material can be incorporated into one or more of the layers of balloon 102. A compatibilizing material may reduce slippage between adjacent layers (e.g., layers 106 and 108) by enhancing the homogeneity of the melt blend prior to extrusion and cooling. For example, the compatibilizing material may be added to a pre-extruded melt blend to provide a more indistinct phase boundary between adjacent layers. Examples of compatibilizing materials include copolyester elastomers, ethylene unsaturated ester copolymers, such as ethylene-maleic anhydride copolymers, copolymers of ethylene and a carboxylic acid or acid derivative, such as ethylene-methyl acrylate copolymers, polyolefins or ethylene-unsaturated ester copolymers grafted with functional monomers, such as ethylene-methyl acrylate copolymers, copolymers of ethylene and a carboxylic acid or acid derivative, such as ethylene-methyl acrylate maleic anhydride terpolymers, terpolymers of ethylene, unsaturated ester and a carboxylic acid or acid derivative, such as ethylene-methyl acrylate-methacrylic acid terpolymers, maleic acid grafted styrene-ethylene-butadiene-styrene block copolymers, and acrylic acid elastomers, such as acrylic rubbers. Similar polymers containing epoxy functional groups, for instance derived from glycidyl methylacrylate (e.g., alkyl(meth)acrylate-ethylene-glycidyl(meth)acrylate polymers) can be used. Ionomeric copolymers can be used. PETG can be used. Examples of compatibilizing materials include Hytrel HTR-6108, Polybond 3009 (BP Chemicals), SP 2205 (Chevron), DS 1328/60 (Chevron), Lotader 2400, EscorATX-320, EscorATX-325, Vamac G1 and Lotader AX8660. In certain embodiments, a compatibilizing material (e.g., PETG) can be mixed with one or more polymers (e.g., an LCP-containing material) prior to extrusion. Other compatibilizing materials can also be used. Combinations of compatibilizing materials can similarly be used.

In certain embodiments, first layer 106 and/or second layer 108 have a minimum thickness of at least about one micron (e.g., at least about 1.5 microns, at least about two microns, at least about 2.5 microns, at least about three microns, at least about 3.5 microns, at least about five microns, at least about ten microns, at least about 15 microns, at least about 20 microns, at least about 25 microns, at least about 30 microns, at least about 35 microns, at least about 40 microns, at least about 45 microns) and/or a maximum thickness of at most about 50 microns (e.g., at most about 45 microns, at most about 40 microns, at most about 35 microns, at most about 30 microns, at most about 25 microns, at most about 20 microns, at most about 15 microns, at most about 10 microns, at most about five microns, at most about 3.5 microns, at most about three microns, at most about 2.5 microns, at most about two microns, at most about 1.5 microns).

The thicknesses of first layer 106 and second layer 108 may be different or the same. In some embodiments, first layer 108 makes up from about one percent to about 50% (e.g., from about 5% to about 50%, from about 5% to about 40%, about 30% or less, from about 20% to about 30%) of the total tube or balloon wall thickness, and second layer 108 makes up the balance. In certain embodiments, second layer 108 makes up from about one percent to about 50% (e.g., from about 5% to about 50%, from about 5% to about 40%, about 30% or less, from about 20% to about 30%) of the total tube or balloon wall thickness and first layer 106 makes up the balance.

In some embodiments, one or more of the materials from which balloon 102 (e.g., layers 106 and 108 of balloon 102) is formed are relatively soft and flexible. This can help to provide balloon 102 with good re-fold characteristics (e.g., after the balloon has been inflated and deflated) and good trackability and crossability through a body lumen. In certain embodiments, for example, balloon 102 (e.g., the materials from which balloon 102 is formed) has a compliancy of about one percent or greater (e.g., about five percent or greater, about ten percent or greater) over a predetermined pressure range (e.g., from atmospheric pressure to a rated burst pressure). Balloon 102 can have a rated burst pressure of about ten atmospheres to about 30 atmospheres.

While balloon 102 is shown as having four cutting elements 105, balloon 102 can have various numbers of cutting elements 105. Balloon 102 can, for example, have one (e.g., 2, 3, 4, 5, 6, 7, 8) or more cutting elements 105. Cutting elements 105 can be equally and/or unequally spaced around the circumference of balloon 102. Cutting elements 105 can extend continuously and/or non-continuously along portions of balloon 102. For example, a cutting element line can be formed of a plurality of cutting elements arranged end to end. Combinations of different spacings, configurations and/or dimensions are possible. Cutting elements 105 can have smooth and/or jagged, e.g., serrated, cutting edges. In some embodiments, cutting elements 105 are formed of a metal. As described above, for example, cutting elements 105 can be steel blades. Cutting elements 105 can alternatively or additionally be formed of a polymer having sufficient hardness, stiffness, and/or strength. A polymeric cutting element may include an LCP. A polymeric cutting element may be formed (e.g., by molding) and then attached to balloon 102 using an adhesive. Any of various other suitable materials can alternatively or additionally be used to form cutting elements 105.

Balloon 102 can be formed from a tube or parison formed by an extrusion process, such as by disc co-extrusion. An example of disc co-extrusion is described in Patent Application Publication No. US 2002-0165523 A1.

To form balloon 102, the formed (e.g., co-extruded) tube can be blow molded. In some embodiments, the tube is placed in a preheated balloon mold, and air is introduced into the tube to maintain the patency of the tube lumen. After soaking at a predetermined temperature and time, the tube is stretched for a predetermined distance at a predetermined time, rate, and temperature. The pressure inside the tube is then sufficiently increased to radially expand the tube inside the mold to form the balloon. The formed balloon can be heat treated, for example, to enhance folding memory, and/or folded into a predetermined profile. Methods of forming a balloon from a tube are described in, for example, commonly-assigned U.S. Ser. No. 09/950,195, filed Sep. 10, 2001, and entitled "Medical Balloon," now abandoned; U.S. Pat. Nos. 6,120,364; 5,714,110; and 4,963,313, all hereby incorporated by reference in their entirety.

Figure 3:
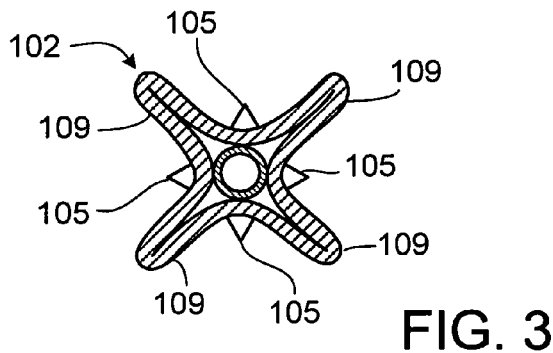
FIG. 3 is a cross-sectional view of the balloon catheter of FIG. 1.
Figure 4:
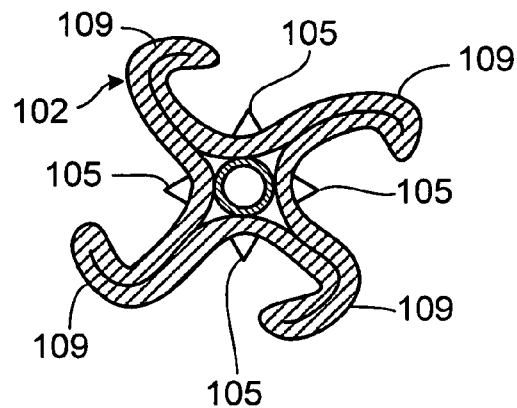
FIG. 4 is a cross-sectional view of the balloon catheter of FIG. 1.

After the balloon is formed, cutting elements can be attached (e.g., adhesively attached) to the balloon to form balloon 102. Balloon 102 can then be folded (FIG.3) using methods described, for example, in U.S. Pat. No. 5,209,799. In some cases, relatively compliant areas (e.g., flaps 109) of balloon 102 can be folded over cutting elements 105 to protect a body lumen from the cutting edges of cutting elements 105. Folding can be performed by engaging (e.g., grasping) flaps 109 with a chuck, and rotating the chuck. Folding can be performed during heat treatment of balloon 102, as described in U.S. Pat. No. 5,209,799.

While a number of embodiments have been described above, other embodiments are possible.

As an example, while first layer 106 has been described as having a lower modulus of elasticity than second layer 108, in some embodiments, first layer 106 has a higher modulus of elasticity than second layer 108.

As another example, while first layer 106 has been described as being softer than second layer 108, in some embodiments, first layer 106 is harder than second layer 108. In certain embodiments, first layer 106 and second layer 108 are substantially equal in hardness.

Figure 5:
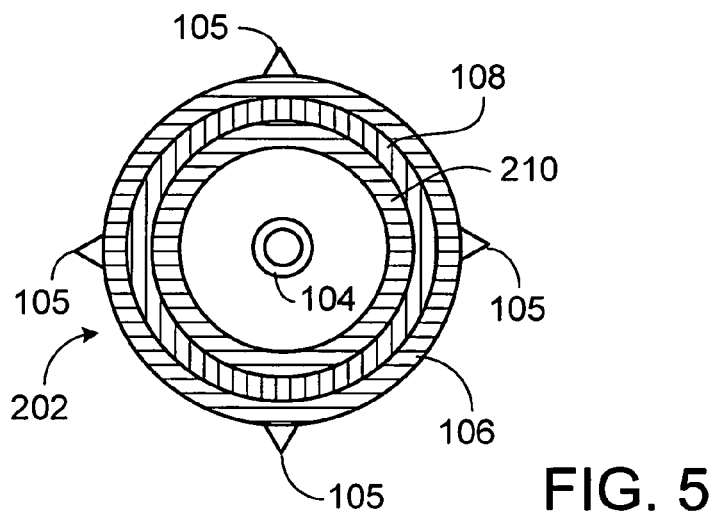
FIG. 5 is a cross-sectional view of an embodiment of a balloon catheter.

As an additional example, while the inflatable balloon of the embodiments above was described as having two layers, in some embodiments, the balloon includes three or more layers. FIG.5, for example, shows a three-layer balloon 202 that can be formed using a technique similar to those described herein. Balloon 202 includes a third layer 210 that is disposed inwardly of second layer 108. Certain physical properties of third layer 210 differ from adjacent second layer 108. In some embodiments, third layer 210 has a modulus of elasticity that differs from the modulus of elasticity of second layer 108 by at least about 2,000 psi (e.g., at least about 5,000 psi, at least about 10,000 psi, at least about 25,000 psi, at least about 50,000 psi, at least about 75,000 psi, at least about 100,000 psi). The modulus of elasticity of second layer 108 can, for example, differ from the modulus of elasticity of third layer 210 by at least about 50 percent (e.g., 100 percent, 150 percent, 200 percent, 250 percent, 300 percent, 350 percent, 400 percent, 450 percent, 500 percent) of the modulus of elasticity of third layer 210. The modulus of elasticity of third layer 210 may be greater than or less than the modulus of elasticity of second layer 108. In certain embodiments, the modulus of elasticity of third layer 210 is substantially equal to the modulus of elasticity of first layer 106. In some embodiments, for example, third layer 210 is formed of the same material as first layer 106 in some embodiments. The modulus of elasticity of third layer 210 can, however, differ from the modulus of elasticity of first layer 106.

Third layer 210 can be formed of any of the various materials described above with respect to first and second layers 106 and 108. In some embodiments, first, second, and third layers 106, 108, and 210 are formed of Pebax, nylon, and Pebax, respectively. In certain embodiments, first, second, and third layers 106, 108, and 210 are formed of nylon, PET, and nylon, respectively. In some embodiments, first, second, and third layers 106, 108, and 210 are formed of Pebax, Nylon 6, and Nylon 12, respectively.

The balloon catheters described herein can include a balloon having four (e.g., five, six, seven, eight, nine, ten, 11, 12, 13, 14, 15, 16) or more layers. The modulus of elasticity of adjacent layers within the balloon, as with the embodiments described above, can differ from one another. In certain embodiments, the moduli of elasticity of each of the adjacent layers differ by at least about 2,000 psi (e.g., at least about 5,000 psi, at least about 10,000 psi, at least about 25,000 psi, at least about 50,000 psi, at least about 75,000 psi, at least about 100,000 psi), and/or by at least about 50 percent (e.g., 100 percent, 150 percent, 200 percent, 250 percent, 300 percent, 350 percent, 400 percent, 450 percent, 500 percent) of the modulus of elasticity of one of the adjacent layers. In some embodiments, the moduli of elasticity of the layers progressively increase from the innermost layer to the outer most layer. In certain embodiments, the moduli of elasticity of the layers progressively decrease from the innermost layers to the outermost layers. In some embodiments, the layers of the balloon are arranged in an alternating pattern such that the moduli of elasticity of the layers fluctuate across the thickness of the balloon wall.

Similar to the modulus of elasticity, the hardness of the layers can progressively increase or decrease from the innermost layer to the outermost layer. The layers can alternatively or additionally be arranged so that the hardness of the layers fluctuates across the thickness of the balloon wall. The thickness of the layers can similarly vary. The thickness of the layers may, for example, vary progressively across the thickness of the balloon wall. For example, the layers may progressively become thicker from the outermost layer to the innermost layer or vice versa. In certain embodiments, the thickness of some of the layers vary across the thickness of the balloon wall while thickness of other layers remains constant.

As a further example, while cutting elements 26 were described above as being adhesively attached to the balloon, other methods of attaching cutting elements 26 to the balloon (e.g., to the outer layer of the balloon) are possible. Cutting elements 26 can, for example, be thermally and/or mechanically bonded. Alternatively or addtionally, cutting elements 26 can include projections, e.g., hooks, at their base that embed into the wall of the balloon. The projections can be embedded manually. The cutting elements can be appropriately positioned in the balloon-forming mold with the projections extending into the cavity of the mold. The projections can be embedded into the wall of the balloon as a tube is radially expanded to form the balloon.

Figure 6:
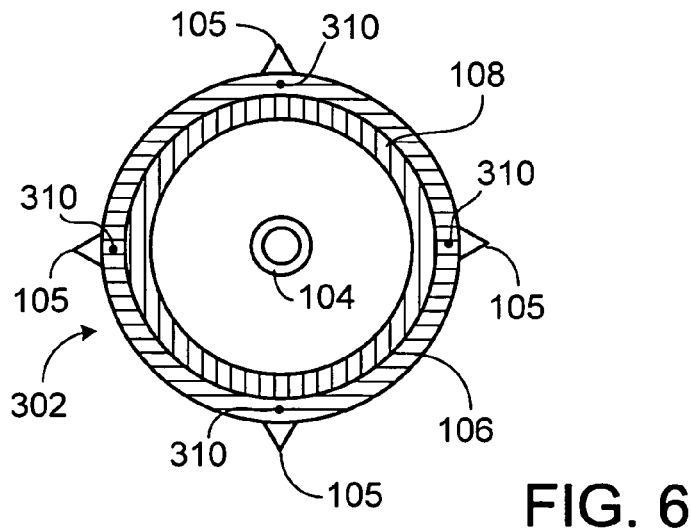
FIG. 6 is a cross-sectional view of an embodiment of a balloon catheter.

As another example, in some embodiments, the inflatable balloon includes striped portions that extend through one or more of its layers. Referring to FIG.6, for example, a balloon 302 is co-extruded to include first layer 106, second layer 108, and striped portions 310 (here, four) extending through first layer 106. Cutting elements 105 are attached to balloon 302 over striped portions 310. In certain embodiments, striped portions 310 are formed of a material(s) having a lower compliancy than the material(s) from which first layer 106 is formed. Alternatively or additionally, striped portions 310 can be formed of one or more materials having a lower distensibility than the material(s) from which first layer 106 is formed. Compliancy and distensibility may apply to the radial direction and/or the longitudinal direction of balloon 302. In some embodiments, striped portions 310 are stiffer, harder, and/or stronger than first layer 106.

Attaching cutting elements 105 over striped portions 310 can enhance the attachment between the cutting elements and balloon 302. For example, as balloon 302 is inflated (e.g., up to 10 atm or higher) and deflated during use, striped portions 310 are less likely to change, e.g., grow or distend, longitudinally and/or radially, relative to first layer 106. The interface between cutting elements 105 and striped portions 310 can remain relatively constant during use. As a result, mechanical stress between cutting elements 105 and balloon 302 can be reduced, and the attachment therebetween can be enhanced.

Striped portions 310 can also enhance folding and refolding of balloon 302. Striped portions 310 and areas adjacent to the striped portions can behave like hinges. For example, a (relatively non-compliant) striped portion 310 can act as a stationary member of a hinge and the (relatively compliant)

adjacent areas can act as moveable members of the hinge that pivot about the interfacial region between the striped portion and the adjacent areas. When balloon 302 is deflated, it can fold along the interfacial region so that compliant areas form flaps, and striped portions 310 are positioned in furrows. As a result, balloon 302 can be formed and used with a relatively low profile and a relatively predictable folding configuration, thereby providing desirable insertion and withdrawal of the balloon catheter from a subject. Embodiments of balloon 302 and stripes portions 310 are described in Patent Application Publication No. US 2003-0163148 A1, which is incorporated by reference herein.

While striped portions 310 have been described as extending through first layer 106, striped portions 310 can alternatively or additionally extend through other regions of balloon 302 (e.g., through second layer 108).

As an additional example, in some embodiments, the balloon includes features to enhance its ability to fold and/or to promote rupture in a preferred direction (e.g., in a direction parallel to the longitudinal axis of the balloon). Examples of balloons including such features are described in U.S. patent application Ser. No. 11/060,151, filed Feb. 17, and entitled "Medical Devices," which is incorporated by reference herein.

The following examples illustrate processes for forming multi-layer balloons:

EXAMPLE 1

First and second materials are co-extruded to form a tube including two layers, a first layer (i.e., an outer layer) and a second layer (i.e., an inner layer). The tube has an outer diameter of 0.058 inch (about 1.5 millimeters) and an inner diameter of 0.032 inch (about 0.8 millimeter). The first layer of the tube is extruded from Pebax 7233 pellets (Manufactured by Arkema Inc. of Philadelphia, Pa.), and the second layer of the tube is extruded from Nylon 12 Vestamid L2101F pellets (Manufactured by Degussa Corp. of Parsippany, N.J.). The first and second layers are extruded using first and second extruders, respectively. The first layer is extruded at a melt temperature of 360° F. (about 182° C.) while the second layer is extruded at 360-390° F. (about 182-199° C.). The extrusion is performed with a contact cooling temperature of about 80° F. (about 27° C.) and a line speed of 55 fpm (about 16.8 meters per minute).

The extruded tube is then placed in a 5 millimeter by 10 millimeter balloon mold that has been preheated to a temperature of 285° F. (about 141° C.). The tube is then held at both of its ends, and air is injected into the tube at about 280 psi (about 1.93 MPa) to prevent the tube from collapsing under the heat. The tube is heated in the mold for about 50 seconds, and then pulled by both ends at a speed of 10 mm/sec for a distance of 18 millimeters on each end. Each end is then allowed to spring back (e.g., contract) about 1 millimeter. While the tube is pulled, the air pressure inside the tube is increased to about 300 psi (about 2.06 MPa). The tube is then held at 285° F. (about 141° C.) and about 300 psi (about 2.06 MPa) for about 3 seconds. The air pressure is then increased to 380 psi (about 2.62 MPa) and the balloon is maintained at 380 psi (about 2.62 MPa) and 285° F. (about 141° C.) for 10 seconds. The tube is pulled again at its ends for a distance of 12 millimeters at a speed of 10 mm/sec to enhance the balloon tapered cone areas while the pressure is increased from 380 psi (about 2.62 MPa) to 400 psi (about 2.76 MPa) during the second pull. Then the balloon is maintained at about 400 psi (about 2.76 MPa) for 10 seconds to enhance shape memory of the balloon. Then the pressure is dropped to 90 psi (about 0.62 MPa), and then the mold is opened to remove the formed balloon, which has an outer diameter of 5 millimeters.

EXAMPLE 2

First, second, and third materials are co-extruded to form a tube including three layers, a first layer (i.e., an outer layer), a second layer (i.e., a middle layer), and a third layer (i.e., an inner layer). The tube has an outer diameter of 0.092 inch (about 2.3 millimeters) and an inner diameter of 0.052 inch (about 1.3 millimeters). The first layer of the tube is extruded from Pebax 7233 pellets (Manufactured by Arkema Inc. of Philadelphia, Pa.). The second layer of the tube is extruded from Nylon 12 Vestamid L2101F pellets (Manufactured by Degussa Corp. of Parsippany, N.J.). The third layer is extruded from Nylon 12 Vestamid D22 pellets (Manufactured by Degussa Corp., Parsippany, N.J.). The first, second, and third layers are co-extruded using first, second, and third extruders, respectively. The first layer is extruded at a melt temperature of 360° F. (about 182° C.) while the second and third layers are extruded at melt temperatures of 390° F. (about 199° C.) and 400° F. (about 204° C.), respectively. The extrusion is performed with a contact cooling temperature of approximately 80° F. (about 27° C.) and a line speed of 50 fpm (about 16.8 meters per minute).

The extruded tube is then placed in an 8 millimeter by 20 millimeter balloon mold that has been preheated to a temperature of 294° F. (about 146° C.). The tube is then held at both of its ends, and air is injected into the tube at about 340 psi (about 2.34 MPa) to prevent the tube from collapsing under the heat. The tube is heated in the mold for about 60 seconds, and then pulled by both ends at a speed of 10 mm/sec for a distance of 12 millimeters on each end. Each end is then allowed to spring back (e.g., contract) about 1 millimeter. While the tube is pulled, the air pressure inside the tube is increased to about 350 psi (about 2.41 MPa). The tube is then held at 294° F. (about 146° C.) and about 350 psi (about 2.41 MPa) for about 10 seconds. The air pressure remains at 350 psi (about 2.41 MPa) and the balloon is maintained at 350 psi (about 2.41 MPa) and 294° F. (about 146° C.) for 20 seconds. Then the tube is pulled again for a distance of 5 millimeters at a speed of 10 mm/sec to enhance the balloon tapered cone areas while the pressure is increased from 350 psi (about 2.41 MPa) to 360 psi (about 2.48 MPa). The balloon is then maintained at about 360 psi (about 2.48 MPa) for 20 seconds to enhance shape memory of the balloon. The pressure is then dropped to 70 psi (about 0.48 MPa) and the mold is opened to remove the formed balloon, which has an outer diameter of 8 millimeters.

All publications, applications, and patents mentioned in this application are herein incorporated by reference to the same extent as if each individual publication or patent was specifically and individually indicated to be incorporated by reference.

Other embodiments are within the claims.

What is claimed is:

1. A medical device comprising:
    an inflatable balloon comprising
        a first layer comprising a material having a first modulus of elasticity;
        a second layer adjacent the first layer, the second layer comprising a material having a second modulus of elasticity greater than the first modulus of elasticity, the second modulus of elasticity in the range of about 200,000 psi to about 600,000 psi, wherein the second modulus of elasticity differs from the first modulus of elasticity by at least about 50,000 psi;

a cutting element attached to the balloon; and a layer of adhesive disposed between the cutting element and an outer surface of the first layer;

wherein the first layer is disposed outwardly of the second layer such that the first layer absorbs and distributes stresses imposed by the cutting element and the second layer provides high burst strength and low distention; and wherein each of the first and second layers has a thickness of at least 30 microns.

2. The medical device of claim 1, wherein the second modulus of elasticity differs from the first modulus of elasticity by at least about 50 percent of the first modulus of elasticity.

3. The medical device of claim 1, wherein an inner surface of the first layer is attached to an outer surface of the second layer.

4. The medical device of claim 3, wherein the inner surface of the first layer is bonded to the outer surface of the second layer.

5. The medical device of claim 3, wherein the inner surface of the first layer is adhesively attached to the outer surface of the second layer.

6. The medical device of claim 1, wherein the first layer has a hardness less than a hardness of the second layer.

7. The medical device of claim 1, wherein the first modulus of elasticity is less than the second modulus of elasticity.

8. The medical device of claim 1, wherein the cutting element is secured to an outer surface of the first layer.

9. The medical device of claim 1, further comprising at least a third layer disposed inwardly of the second layer, the third layer having a third modulus of elasticity that differs from the second modulus of elasticity by at least about 2,000 psi.

10. The medical device of claim 9, wherein the third modulus of elasticity is less than the second modulus of elasticity.

11. The medical device of claim 1, wherein the thickness of the second layer is greater than the thickness of the first layer.

12. The medical device of claim 1, wherein the thicknesses of the first and second layers are substantially equal.

13. The medical device of claim 1, wherein the inflatable balloon comprises at least five layers.

14. The medical device of claim 13, wherein each of the at least five layers has a modulus of elasticity that differs from an adjacent layer by at least about 2,000 psi.

15. The medical device of claim 1, wherein the inflatable balloon has a burst pressure of about ten atmospheres to about 30 atmospheres.

16. The medical device of claim 1, wherein the inflatable balloon has compliance of about one percent to about 15 percent.

\* \* \* \* \*